(12) United States Patent
Baik et al.

(10) Patent No.: US 11,913,858 B2
(45) Date of Patent: Feb. 27, 2024

(54) DISC-SHAPED SAMPLE CHAMBER AND PROBE INCLUDING THE SAME

(71) Applicants: WOOJIN Electro-Nite Inc., Pyeongtaek-si (KR); Heraeus Electro-Nite International N.V., Houthalen (BE)

(72) Inventors: Bong-Ki Baik, Pyeongtaek-si (KR); Young-jin Jung, Pyeongtaek-si (KR); Cheol-jung Kim, Pyeongtaek-si (KR)

(73) Assignee: HERAEUS ELECTRO-NITE INTERNATIONAL N.V., Houthalen (BE)

( * ) Notice: Subject to any disclaimer, the term of this patent is extended or adjusted under 35 U.S.C. 154(b) by 0 days.

(21) Appl. No.: 17/757,867

(22) PCT Filed: Dec. 11, 2020

(86) PCT No.: PCT/EP2020/085668
§ 371 (c)(1),
(2) Date: Jun. 22, 2022

(87) PCT Pub. No.: WO2021/130027
PCT Pub. Date: Jul. 1, 2021

(65) Prior Publication Data
US 2023/0026127 A1    Jan. 26, 2023

(30) Foreign Application Priority Data
Dec. 27, 2019  (KR) .......................... 10-2019-0176990

(51) Int. Cl.
*G01N 1/12*      (2006.01)
*G01N 33/205*    (2019.01)
*C21C 5/46*      (2006.01)

(52) U.S. Cl.
CPC ........... *G01N 1/125* (2013.01); *G01N 33/205* (2019.01); *C21C 5/4673* (2013.01)

(58) Field of Classification Search
CPC .... G01N 1/125; G01N 33/205; G01N 1/1409; G01N 1/02; C21C 5/4673
(Continued)

(56) References Cited

U.S. PATENT DOCUMENTS 3,859,857 A * 1/1975 Falk ........................ G01N 1/125
                                                    73/864.57
3,877,309 A    4/1975 Hance
(Continued)

FOREIGN PATENT DOCUMENTS

EP    0114688 A2   8/1984
EP    3336511 A1   6/2018
(Continued)

*Primary Examiner* — Robert R Raevis
(74) *Attorney, Agent, or Firm* — Blank Rome LLP

(57) ABSTRACT

Disclosed is a disc-shaped sample chamber for collecting molten metal, the chamber comprising: a chamber body having a left body and a right body bonded to each other to define a disc-shaped sample space therebetween; an inlet extending upward from the chamber body and connecting the sample space with the outside; and a welded bonding portion disposed on at least one lateral face of the chamber body for bonding the left body and the right body to each other. Further, a probe having the chamber is disclosed.

13 Claims, 6 Drawing Sheets

(58) Field of Classification Search
USPC .............. 73/64.56, 864.53–864.59; 266/99
See application file for complete search history.

(56) References Cited

U.S. PATENT DOCUMENTS

| | | | | |
|---|---|---|---|---|
| 3,905,238 A | * | 9/1975 | Falk | ............ G01N 1/1409 |
| | | | | 73/864.54 |
| 4,010,649 A | * | 3/1977 | Falk | ............ G01N 1/125 |
| | | | | 73/864.58 |
| 4,067,242 A | | 1/1978 | Judge | |

FOREIGN PATENT DOCUMENTS

| | | | |
|---|---|---|---|
| JP | S5879262 A | 5/1983 | |
| JP | 2018044955 A | 3/2018 | |
| KR | 10-2011-0138145 A | 12/2011 | |
| RU | 172338 U1 | 7/2017 | |
| WO | WO-2019071137 A1 * | 4/2019 | ............ B22D 2/00 |

* cited by examiner

[FIG. 1]
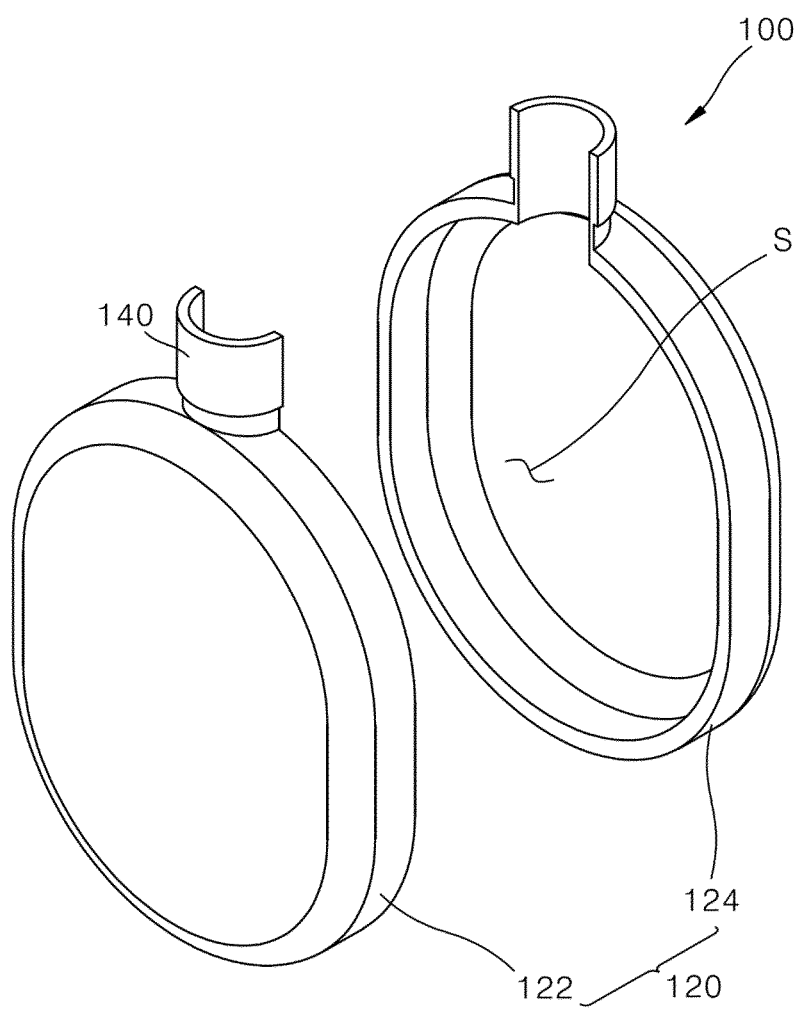

[FIG. 2]
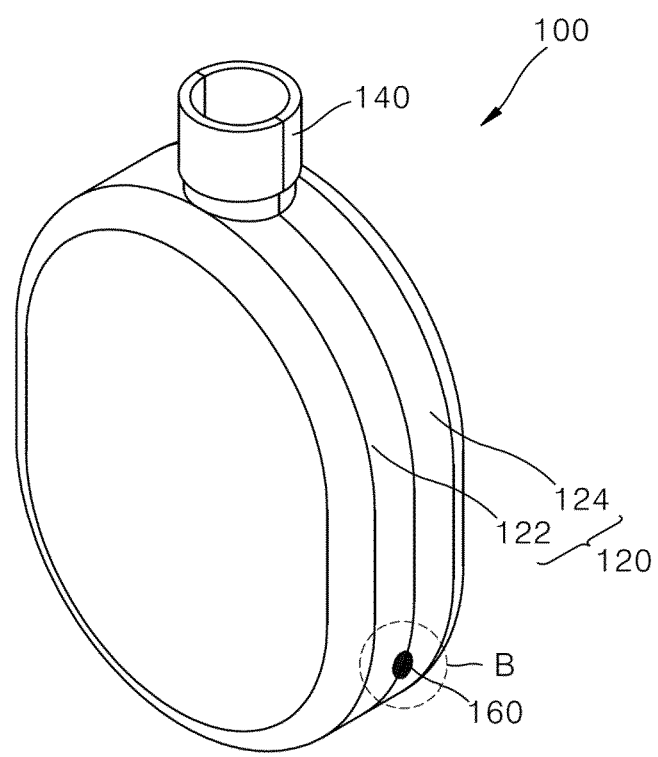

[FIG. 3]
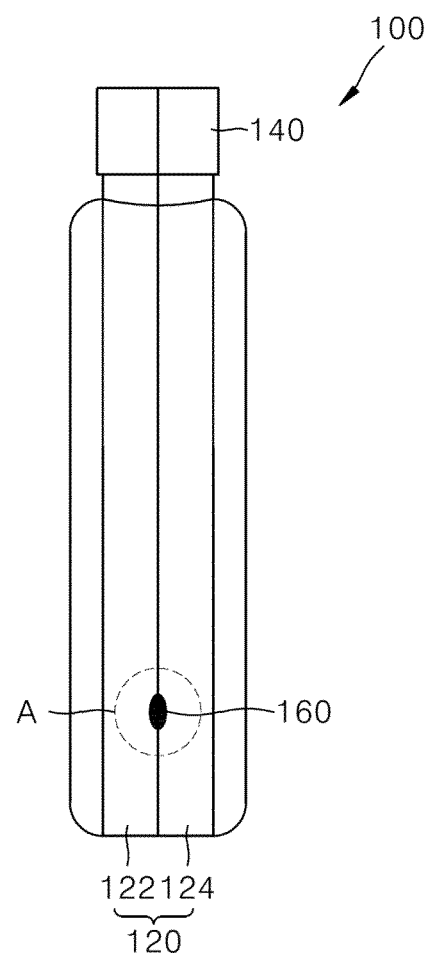

[FIG. 4]
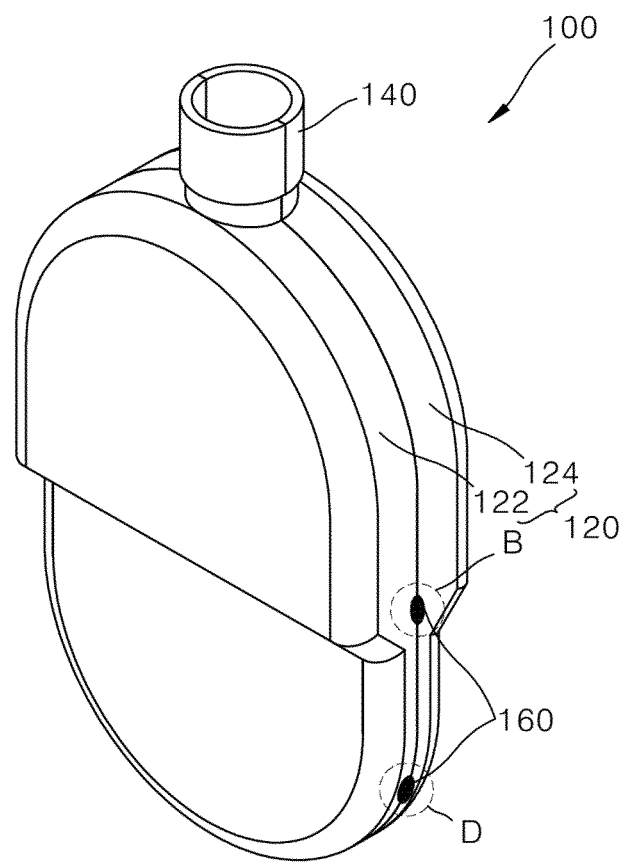

[FIG. 5]
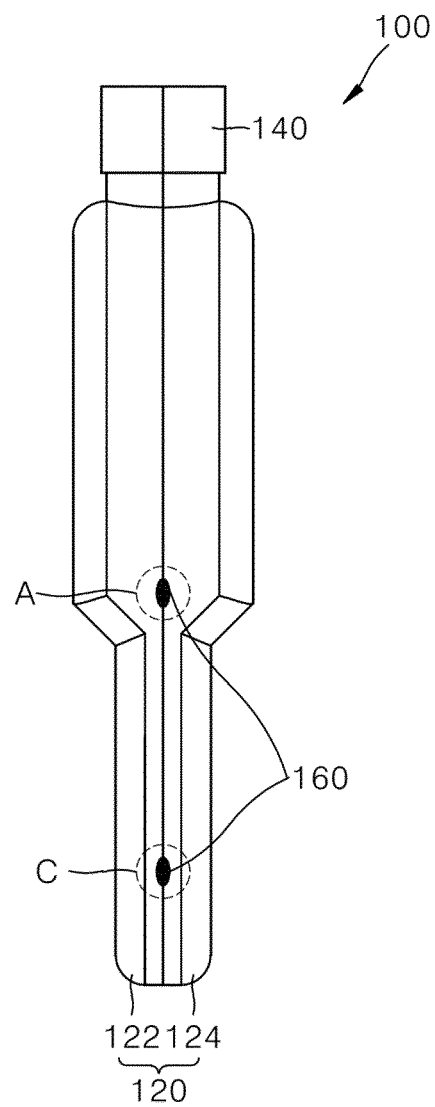

[FIG. 6]
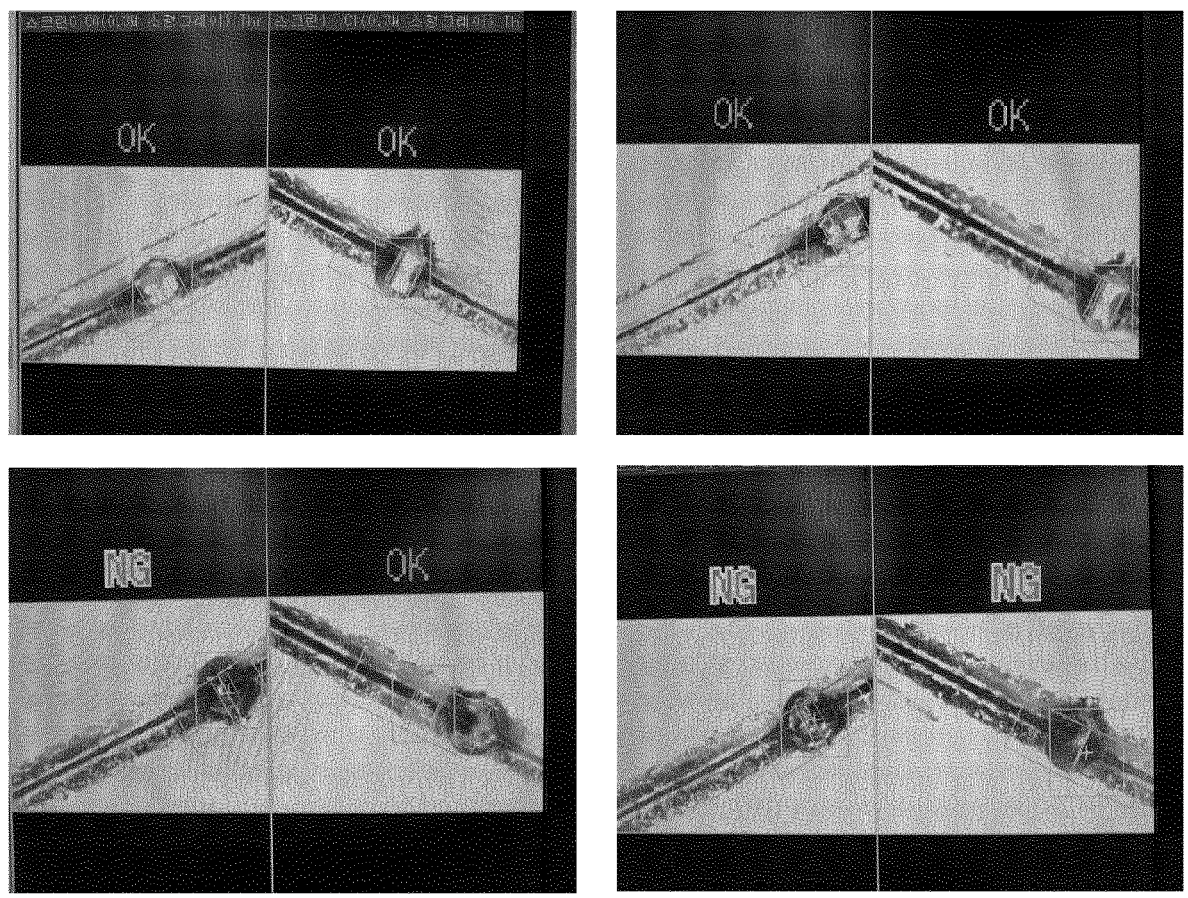
[FIG. 7]
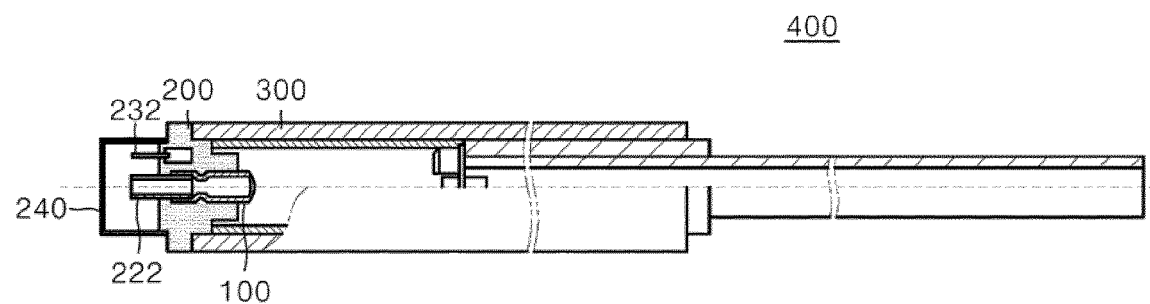

DISC-SHAPED SAMPLE CHAMBER AND PROBE INCLUDING THE SAME

BACKGROUND

1. Field

The present invention relates to a disc-shaped sample chamber and a probe including the same. More specifically, the present invention relates to a disc-shaped sample chamber in which chamber bodies are bonded to each other on at least one lateral face thereof using a spot welding scheme, and to a probe including the chamber.

2. Description of Related Art

In a steel making process, various efforts are being made to improve the quality of the steel. Accordingly, a molten metal sample is collected and analyzed in order to monitor and control physical properties of the molten metal that affect the purity of the molten steel.

Recently, efforts have been made to collect molten metal samples using various devices. Further, temperature measurement and molten steel sample collection functions are combined to reduce the working time to convert the device into a complex probe.

In general, the probe is used to collect and analyze a certain amount of the molten metal in the steel making process. In a prior art, the molten metal sample is collected by inserting the probe equipped with a disc-shaped sample chamber into an electric furnace.

In general, the disc-shaped sample chamber in the prior art is assembled using a clip for fixating the sample chamber. These clips are generally configured as preloaded springs. When the sample chamber is filled, the expanding gas generates an overpressure which the clip needs to withstand. In cases where the fixation is not strong enough or the sample chambers are not perfectly connected, burrs may form on the sample which are problematic in the further processing and analysis of the resulting samples.

Additionally, a coupling structure using a clip for fixating the sample chamber causes an increase in the costs of the assembled parts of the sample chamber and an additional production time due to the clip coupling. Furthermore, the clip needs to be removed prior to the analysis following taking the sample, which is mostly done manually in combination with special tooling. The additional process step also adds to the cost of this sample closure technique.

A related prior art document includes Korean Patent Application Publication No. 10-2011-0138145 (published Dec. 26, 2011) describing a probe for collecting and measuring a molten metal sample.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present invention is to provide a disc-shaped sample chamber, wherein the chamber bodies are bonded to each other on at least one lateral face thereof using a spot welding scheme, in order to facilitate assembly work and separation of the sample chamber and to reduce production time and cost thereof. Furthermore, a probe including the disc-shaped sample chamber is provided.

A first embodiment of the present invention provides a disc-shaped sample chamber for collecting molten metal, the chamber comprising: a chamber body having a left body and a right body, bonded to each other to define a disc-shaped sample space therebetween; an sample inlet extending upward from the chamber body and connecting the sample space with the outside; and a welded bonding portion positioned on at least one lateral face of the chamber body for bonding the left body and the right body to each other.

In one embodiment of the chamber, a welded bonding portion is positioned at a portion of a bonding line between the left body and the right body, thereby bonding the left body and the right body to each other, wherein the welded bonding portion is formed in a spot welding manner using a laser.

In one embodiment of the chamber, the disc-shaped sample chamber has a vertical dimension higher than or equal to 30 mm and smaller than 100 mm.

Preferably, the vertical dimension is defined along the axis of the sample inlet to the opposite end of the sample chamber.

In one embodiment of the chamber, the disc-shaped sample chamber has a vertical dimension higher than or equal to 30 mm and smaller than 40 mm.

In one embodiment of the chamber, the disc-shaped sample chamber has a vertical dimension higher than or equal to 40 mm and smaller than 57 mm.

In one embodiment of the chamber, the chamber body is vertically divided into two portions, and the welded bonding portion is formed on each of both opposing lateral faces of a lower portion among the two portions.

In one embodiment of the chamber, the welded bonding portion is formed on a curved portion of each of both opposing lateral faces of the lower portion.

In one embodiment of the chamber, the disc-shaped sample chamber has a vertical dimension higher than or equal to 57 mm and smaller than 80 mm.

In one embodiment of the chamber, the chamber body is vertically divided into two portions, and the welded bonding portion is formed on each of both opposing lateral faces of each of lower and middles portions among the three portions.

In one embodiment of the chamber, the welded bonding portion is formed on a curved portion of each of both opposing lateral faces of each of the lower and middle portions.

A second aspect of the present invention provides a probe for collecting molten metal, the probe comprising: a paper tube having a hollow structure having an open front end; a disc-shaped sample chamber fixedly mounted inside a front end portion of the paper tube; a head member mounted into the front end of the paper tube to close the open top of the paper tube; and a sensor member mounted on the head member, wherein the disc-shaped sample chamber includes: a chamber body having a left body and a right body bonded to each other to define a disc-shaped sample space therebetween; an sample inlet extending upward from the chamber body and connecting the sample space with the outside; and a welded bonding portion positioned on at least one lateral face of the chamber body for bonding the left body and the right body to each other.

In one embodiment of the probe, the disc-shaped sample chamber has a vertical dimension higher than or equal to 40 mm and smaller than 57 mm, wherein the chamber body is vertically divided into two portions, and the welded bonding portion is formed on each of both opposing lateral faces of a lower portion among the two portions.

In one embodiment of the probe, the disc-shaped sample chamber has a vertical dimension higher than or equal to 57 mm and smaller than 80 mm, wherein the chamber body is vertically divided into two portions, and the welded bonding portion is formed on each of both opposing lateral faces of each of lower and middles portions among the three portions.

Effects in accordance with the present invention may be as follows but may not be limited thereto.

As described above, according to the present invention, only a portion of the bonding line between the left body and the right body is selectively welded to each other in a laser spot welding scheme, which significantly reduces the assembly time and cost of the sample chamber compared to those when a clip fixing scheme is used.

Further, the coupling scheme between the right and left bodies of the sample chamber is not a clip fixing scheme, but a spot welding scheme using a laser. Thus, assembly and separation of the two bodies of the sample chamber are easy, and the production time and cost for the sample chamber may be reduced.

Further, the welded bonding portion is not formed over the entire bonding line between the left body and the right body, but is selectively placed only at two points or four points respectively on both opposing lateral faces of the chamber body 120 depending the vertical dimension of the sample chamber, thereby allowing the right and left bodies of the chamber body of the sample chamber to be easily separated from each other.

Further, in accordance with the present invention, the size of the welded bonding portion and a contrast measurement value of the bonding line between the two bodies of the sample chamber are estimated using a vision inspection device, and a non-defective product is determined based on the estimation result, thereby improving the production yield.

In addition to the effects described above, specific effects in accordance with the present invention will be described together with the detailed description for carrying out the invention.

BRIEF DESCRIPTIONS OF DRAWINGS

FIG. 1 is a front perspective view showing an exploded state of a disc-shaped sample chamber according to an embodiment of the present invention.

FIG. 2 is a front perspective view showing an assembled state of the disc-shaped sample chamber according to an embodiment of the present invention.

FIG. 3 is a side cross-sectional view showing an assembled state of the disc-shaped sample chamber according to an embodiment of the present invention.

FIG. 4 is a front perspective view showing an assembled state of a disc-shaped sample chamber according to another embodiment of the present invention.

FIG. 5 is a side cross-sectional view showing an assembled state of the disc-shaped sample chamber according to another embodiment of the present invention.

FIG. 6 is a photograph to explain an evaluation process of a welded bonding portion and a bonding line of a sample chamber with a vision inspection device.

FIG. 7 is a cross-sectional view showing a probe including a disc-shaped sample chamber according to an embodiment of the present invention.

DETAILED DESCRIPTIONS

For simplicity and clarity of illustration, elements in the figures are not necessarily drawn to scale. The same reference numbers in different figures represent the same or similar elements, and as such perform similar functionality. Further, descriptions and details of well-known steps and elements are omitted for simplicity of the description. Furthermore, in the following detailed description of the present invention, numerous specific details are set forth in order to provide a thorough understanding of the present invention. However, it will be understood that the present invention may be practiced without these specific details. In other instances, well-known methods, procedures, components, and circuits have not been described in detail so as not to unnecessarily obscure aspects of the present invention.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present invention as defined by the appended claims.

The terminology used herein is for the purpose of describing particular embodiments only and is not intended to limit the present invention. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a disc-shaped sample chamber according to a preferred embodiment of the present invention and a probe including the same will be described in detail with reference to the accompanying drawings.

FIG. 1 is a front perspective view showing an exploded state of a disc-shaped sample chamber according to an embodiment of the present invention. FIG. 2 is a front perspective view showing an assembled state of the disc-shaped sample chamber according to an embodiment of the present invention. FIG. 3 is a side cross-sectional view showing an assembled state of the disc-shaped sample chamber according to an embodiment of the present invention.

Referring to FIG. 1 to FIG. 3, a disc-shaped sample chamber 100 according to an embodiment of the present invention comprises a chamber body 120, a sample inlet 140, and a welded bonding portion 160.

The chamber body 120 includes a left body 122 and a right body 124 which are coupled to each other to define a disc-shaped sample space S defined therebetween. As such, the chamber body 120 is divided into the left body 122 and the right body 124. The left body 122 and the right body 124 are in contact with each other, thereby forming the disc-shaped sample space S defined therebetween.

Each of the left body 122 and the right body 124 has a disk-shaped semicircular structure. the left body 122 and the right body 124 are preferably designed to have a symmetrical structure relative to each other.

The sample inlet 140 extends upward from the chamber body 120 and is formed to communicate the sample space S with the outside. This sample inlet 140 may protrude from a top of the chamber body 120. In this connection, when collecting a molten metal sample, the molten metal sample is introduced into the disc-shaped sample space S through the sample inlet 140.

The welded bonding portion 160 is formed on at least one lateral face of the chamber body 120 to bond the left body 122 and the right body 124 to each other.

More specifically, the welded bonding portion 160 is positioned on a portion of a bonding line between the left body 122 and the right body 124 to bond the left body 122 and the right body 124 to each other, wherein the portion 160 is formed in a spot welding manner using a laser.

The laser based spot welding scheme performs welding by irradiating a laser beam oscillated from a laser oscillator onto welding target points using a laser head. In this connection, the laser head is preferably a scan head capable of irradiating a laser beam to a predetermined scan region, but is not limited thereto.

In this way, only portions of the bonding lines of the left body 122 and the right body 124 are selectively welded to each other in a laser spot welding scheme, thereby significantly reducing the assembly time and cost for the sample chamber compared to those when a clip fixing scheme is used.

The disc-shaped sample chamber 100 according to an embodiment of the present invention has a vertical dimension smaller than 57 mm, and more preferably, the vertical dimension is in a range from 40 mm to 57 mm.

In this case, when the chamber body 120 is divided into an upper portion and a lower portion, the welded bonding portion 160 is preferably formed on each of both opposing lateral faces of the lower portion. In this connection, the welded bonding portion 160 is more preferably formed on a curved portion of each of both opposing lateral faces of the lower portion of the chamber body 120.

Preferably, the welded bonding portion 160 is selectively formed only at each of 2 points A and B on both opposing lateral faces of the lower portion of the chamber body 120, thereby to securely bond the left body 122 and the right body 124 to each other while saving welding time and cost.

In a further embodiment, the welded bonding portion 160 is not formed over the entire bonding line between the left body 122 and the right body 124, but is selectively placed only at each of the 2 points A and B on both opposing lateral faces of the chamber body 120, thereby allowing the right and left bodies of the chamber body of the sample chamber 100 to be easily separated from each other.

In a further embodiment, the diameter of the welded bonding portion 160 is not larger than 15% of the height of the lateral face of the chamber body thereby allowing the right and left bodies of the chamber body of the sample chamber 100 to be easily separated from each other, preferably not larger than 10%, most preferably not larger than 5%.

As described above, according to the present invention, the coupling scheme between the right and left bodies of the sample chamber 100 is not a clip fixing scheme but a spot welding scheme using a laser. Thus, the assembly and separation of the two bodies of the sample chamber 100 may be easy, and production time and cost thereof may be reduced.

FIG. 4 is a front perspective view showing an assembled state of a disc-shaped sample chamber according to another embodiment of the present invention. FIG. 5 is a side cross-sectional view showing an assembled state of the disc-shaped sample chamber according to another embodiment of the present invention. In this connection, FIG. 5 shows a left lateral face of the disc-shaped sample chamber.

As shown in FIG. 4 and FIG. 5, a disc-shaped sample chamber 100 according to another embodiment of the present invention has substantially the same configuration as that of the disc-shaped sample chamber 100 as shown in FIG. 1 to FIG. 3. However, the former has a larger vertical dimension than that of the latter. Thus, duplicate descriptions thereof are omitted, and following descriptions will focus on differences therebetween.

That is, the disc-shaped sample chamber 100 according to another embodiment of the present invention may have a vertical dimension of at least 57 mm, and more preferably, may be in a range of 57 mm to 80 mm. In this connection, when the chamber body 120 is divided into an upper portion, a middle portion and a lower portion, the welded bonding portion 160 may formed on points on both opposing lateral faces of the middle portion and on two points on both opposing lateral faces of the lower portion. In this connection, the welded bonding portion 160 is more preferably formed on a curved portion of each of both opposing lateral faces of the middle portion of the chamber body 120 and a curved portion of each of both opposing lateral faces of the lower portion thereof.

Preferably, the welded bonding portion 160 is selectively formed only at 2 points A and B on both opposing lateral faces of the middle portion of the chamber body 120 and 2 points C and D on both opposing lateral faces of the lower portion thereof, thereby securely bonding the left body 122 and the right body 124 to each other while saving welding time and cost thereof.

Further, the welded bonding portion 160 is not formed over the entire bonding line between the left body 122 and the right body 124, but is selectively placed only at 2 points A and B on both opposing lateral faces of the middle portion of the chamber body 120 and 2 points C and D on both opposing lateral faces of the lower portion thereof, thereby allowing the right and left bodies of the chamber body of the sample chamber 100 to be easily separated from each other.

In a further embodiment, the diameter of the welded bonding portion 160 is not larger than 15% of the height of the lateral face of the chamber body thereby allowing the right and left bodies of the chamber body of the sample chamber 100 to be easily separated from each other, preferably not larger than 10%, most preferably not larger than 5%.

As described above, according to the present invention, the coupling scheme between the right and left bodies of the sample chamber 100 is not a clip fixing scheme but a spot welding scheme using a laser. Thus, the assembly and separation of the two bodies of the sample chamber 100 may be easy, and production time and cost thereof may be reduced.

FIG. 6 is a photograph to explain a process of evaluating the welded bonding portion and the bonding line between the left and right bodies of the sample chamber with a vision inspection device.

In accordance with the present invention, FIG. 6 shows the size of the welded bonding portion and the contrast of the bonding line between the two bodies using a vision inspection device. Only when the measured values satisfy a predefined range, the assembled sample chamber is determined as a non-defective product.

Preferably, when the size of the welded bonding portion measured using the vision inspection device and the contrast of the bonding line between the two bodies of the sample chamber are within a preset range, the assembled sample chamber is determined as a non-defective product.

On the contrary, when the size of the welded bonding portion measured using the vision inspection device and the contrast measurement value of the bonding line between the two bodies of the sample chamber are out of the preset range, the assembled sample chamber is determined as a defective product.

Preferably, in accordance with the present invention, the size of the welded bonding portion and the contrast measurement value of the bonding line between the two bodies of the sample chamber are estimated using a vision inspection device, and the non-defective product is determined based on the estimation result, thereby improving the production yield.

FIG. 7 is a cross-sectional view showing a probe including the disc-shaped sample chamber according to an embodiment of the present invention.

Referring to FIG. 7, the probe 400 including the disc-shaped sample chamber 100 according to an embodiment of the present invention includes a paper tube 300, the disc-shaped sample chamber 100, a head member 200 and a sensor member 232.

The paper tube 300 has a hollow structure with an open front end.

The disc-shaped sample chamber 100 is fixedly mounted inside a front end portion of the paper tube 300. The disc-shaped sample chamber 100 includes the chamber body having a left body and a right body which are bonded to each other to define the disc-shaped sample space therebetween, the sample inlet extending upward from the chamber body and connecting the sample space with the outside, and the welded bonding portion disposed on at least one lateral face of the chamber body for bonding the left body and the right body to each other.

In one embodiment of the chamber, the disc-shaped sample chamber has a vertical dimension higher than or equal to 30 mm and smaller than 100 mm.

Preferably, the vertical dimension is defined along the axis of the sample inlet to the opposite end of the sample chamber.

In one embodiment of the chamber, the disc-shaped sample chamber has a vertical dimension higher than or equal to 30 mm and smaller than 40 mm.

In this connection, the disc-shaped sample chamber 100 according to an embodiment of the present invention has a vertical dimension smaller than 57 mm, and more preferably, the vertical dimension is in a range from 40 mm to 57 mm.

In the case when the chamber body 120 is divided into an upper portion and a lower portion, the welded bonding portion 160 is preferably formed on each of both opposing lateral faces of the lower portion. In this connection, the welded bonding portion 160 is more preferably formed on a curved portion of each of both opposing lateral faces of the lower portion of the chamber body 120.

Preferably, the welded bonding portion 160 is selectively formed only at each of 2 points A and B respectively on both opposing lateral faces of the lower portion of the chamber body 120, thereby to securely bond the left body 122 and the right body 124 to each other while saving the welding time and cost.

Further, the welded bonding portion 160 is not formed over an entirety of the bonding line between the left body 122 and the right body 124, but is selectively placed only at each of the 2 points A and B respectively on both opposing lateral faces of the chamber body 120, thereby to allow the right and left bodies of the chamber body of the sample chamber 100 to be easily separated from each other.

As described above, according to the present invention, the coupling scheme between the right and left bodies of the sample chamber 100 is not the clip fixing scheme but the spot welding scheme using a laser. Thus, the assembly and separation of the two bodies of the sample chamber 100 may be easy, and the production time and cost thereof may be reduced.

Alternatively, the disc-shaped sample chamber 100 according to another embodiment of the present invention may have a vertical dimension of at least 57 mm, and more preferably, may be in a range of 57 mm to 80 mm. In this connection, when the chamber body 120 are divided into an upper portion, a middle portion and a lower portion, the welded bonding portion 160 may formed on points respectively on both opposing lateral faces of the middle portion and on two points respectively on both opposing lateral faces of the lower portion. In this connection, the welded bonding portion 160 is more preferably formed on a curved portion of each of both opposing lateral faces of the middle portion of the chamber body 120 and a curved portion of each of both opposing lateral faces of the lower portion thereof.

Preferably, the welded bonding portion 160 is selectively formed only at 2 points A and B on both opposing lateral faces of the middle portion of the chamber body 120 and 2 points C and D on both opposing lateral faces of the lower portion thereof, thereby securely bonding the left body 122 and the right body 124 to each other while saving welding time and cost.

Further, the welded bonding portion 160 is not formed over the entire bonding line between the left body 122 and the right body 124, but is selectively placed only at 2 points A and B on both opposing lateral faces of the middle portion of the chamber body 120 and 2 points C and D on both opposing lateral faces of the lower portion thereof, thereby allowing the right and left bodies of the chamber body of the sample chamber 100 to be easily separated from each other.

As described above, according to the present invention, the coupling scheme between the right and left bodies of the sample chamber 100 is not a clip fixing scheme but a spot welding scheme using a laser. Thus, the assembly and separation of the two bodies of the sample chamber 100 may be easy, and the production time and cost thereof may be reduced.

The head member 200 is mounted at the front end of the paper tube 300 to close the open end of the paper tube 300. The head member 200 may further include a protective cap 240 that is positioned at the front end thereof to protect the sample chamber 100 and the sensor member 232 from the outside. In this connection, the sample chamber 100 may be fixed to the head member 200 via a connector member 222. The connector member 222 may be inserted into the sample inlet of the sample chamber 100 and an opening of the head member 200.

The sensor member 232 is mounted on the head member 200. The sensor member 232 may be fixedly installed on the head member 200 to measure a temperature and an oxygen content of the molten metal.

The probe 400 including the disc-shaped sample chamber according to an embodiment of the present invention described above may be used for collecting various types of molten metals. In particular, the probe may be mainly used for the collection of molten metal from an electric furnace in an immersed manner.

As described above, according to the present invention, only a portion of the bonding line between the left body and the right body is selectively welded to each other in a laser spot welding scheme, thereby significantly reducing the assembly time and cost of the sample chamber compared to those when a clip fixing scheme is used.

Preferably, the coupling scheme between the right and left bodies of the sample chamber is not a clip fixing scheme but a spot welding scheme using a laser. Thus, the assembly and separation of the two bodies of the sample chamber are easy, and production time and cost thereof may be reduced.

Further, the welded bonding portion is not formed over the entire bonding line between the left body and the right body, but is selectively placed only at each of the two points or four points respectively on both opposing lateral faces of the chamber body 120 depending the vertical dimension of the sample chamber, thereby allowing the right and left bodies of the chamber body of the sample chamber to be easily separated from each other.

Preferably, in accordance with the present invention, the size of the welded bonding portion and the contrast measurement value of the bonding line between the two bodies of the sample chamber are estimated using a vision inspection device, and a non-defective product is determined based on the estimation result, thereby improving the production yield.

As described above, the present invention is described with reference to the drawings. However, the present invention is not limited to the embodiments and drawings disclosed in the present specification. It will be apparent that various modifications may be made thereto by those skilled in the art within the scope of the present invention. Furthermore, although the effect resulting from the features of the present invention has not been explicitly described in the description of the embodiments of the present invention, it is obvious that a predictable effect resulting from the features of the present invention should be recognized.

In the following, exemplary conditions according to the invention will be given.

A sample chamber comprising two sample chamber body halves made from steel according to FIG. 2 with a length of 60 mm, a width of 32 mm and a height of 12 mm were welded together at two points. The welding points had a diameter of 1.3 mm.

Test and Evaluation of Bonding Strength of Welded Joints
Shear Strength

The strength of the welded connection was evaluated in a shear test. The assembled sample chamber was placed in a tensile testing machine (type Tinius Olsen H10KT) at a constant cross head speed of 1.5 mm/min parallel to the joining line between the sample chamber body halves. The maximum force to disconnect the welded seam was determined.

The shear force was in the range of 100-450 N for sample chambers according to the invention.

Resistance Against Breaking

In an alternative method to test the strength of the welded connection, the minimum fall height to break the weld connection of a sample chamber was determined. An unfilled welded sample chamber was placed in a certain height above a concrete surface and dropped on the surface. The minimum fall height needed to break a connection of the sample after the fall is a representative measure for the strength of the connection. The higher this minimum fall height, the stronger the connection.

For the exemplary sample chamber, this height was 40 cm. In comparison, a traditional sample chamber with a clip will not open in such a test.

A minimum drop height of 20 cm needs to be guaranteed without breaking, while 40 cm is considered a representative height for a sample chamber, which is suitable for the further processing after filling with the molten metal sample.

What is claimed is:

1. A sample chamber for collecting molten metal, the chamber comprising:
   a chamber body having a left body and a right body bonded to each other to define a sample space therebetween;
   a sample inlet extending upward from the chamber body and connecting the sample space with the outside; and
   at least one welded bonding portion disposed on at least one lateral face of the chamber body bonding the left body and the right body to each other,
   wherein the welded bonding portion is located at a portion of a bonding line between the left body and the right body and the welded bonding portion is formed by spot welding the left body and the right body to each other at the portion of the bonding line.

2. The sample chamber of claim 1, wherein the sample space has a vertical dimension higher than or equal to 40 mm and smaller than 57 mm, wherein the vertical dimension is defined by a vertical axis extending from the sample inlet to a lower end of the sample chamber.

3. The sample chamber of claim 2, wherein the chamber body comprises an upper portion, a middle portion and a lower portion, wherein
   the upper portion, the middle portion, and the lower portion are defined relative to the vertical axis, and
   the sample chamber comprises two welded bonding portions, each located on opposing lateral faces of the lower portion.

4. The sample chamber of claim 3, wherein the two welded bonding portions are located on curved portions of the opposing lateral faces of the lower portion.

5. The sample chamber of claim 1, wherein the sample chamber has a vertical dimension higher than or equal to 57 mm and smaller than 80 mm, wherein the vertical dimension is defined by a vertical axis extending from the sample inlet to a lower end of the sample chamber.

6. The sample chamber of claim 5, wherein the chamber body is vertically divided into an upper portion, a middle portion and a lower portion, wherein
   the upper portion, the middle portion, and the lower portion are defined relative to the vertical axis,
   the sample chamber comprises four welded bonding portions with two of the welded bonding portions located on opposing lateral faces of the middle portion and two of the welded bonding portions located on opposing lateral faces of the lower portion.

7. The sample chamber of claim 6, wherein the chamber body is vertically divided into an upper portion, a middle portion and a lower portion, wherein
   the upper portion, the middle portion, and the lower portion are defined relative to the vertical axis,
   the sample chamber comprises four welded bonding portions with two of the welded bonding portions located on curved portions of opposing lateral faces of the middle portion and two of the welded bonding portions located on curved portions of opposing lateral faces of the lower portion.

8. A probe for collecting molten metal, the probe comprising:
   a paper tube having a hollow structure having an open front end;
   a sample chamber according to claim 1 fixedly mounted inside a front end portion of the paper tube;
   a head member mounted into the front end of the paper tube to close the open top of the paper tube; and
   a sensor member mounted on the head member.

9. The probe of claim 8, wherein the sample chamber has a vertical dimension higher than or equal to 40 mm and smaller than 57 mm, the vertical dimension defined by a vertical axis extending from the sample inlet to a lower end of the sample chamber, wherein
   the chamber body comprises an upper portion, a middle portion and a lower portion, the upper portion, the middle portion, and the lower portion defined relative to the vertical axis, and
   the sample chamber comprises two welded bonding portions, each located on opposing lateral faces of the lower portion.

10. The probe of claim 8, wherein the sample chamber has a vertical dimension higher than or equal to 57 mm and smaller than 80 mm, the vertical dimension defined by a vertical axis extending from the sample inlet to a lower end of the sample chamber, wherein
    the chamber body comprises an upper portion, a middle portion and a lower portion, the upper portion, the middle portion, and the lower portion defined relative to the vertical axis, and
    the sample chamber comprises four welded bonding portions with two of the welded bonding portions located on opposing lateral faces of the middle portion and two of the welded bonding portions located on opposing lateral faces of the lower portion.

11. The sample chamber of claim 1, wherein the spot welding is performed using a laser.

12. The sample chamber of claim 1, wherein the left side and the right side are symmetrical.

13. The sample chamber of claim 1, wherein the sample chamber is made of steel.

* * * * *